(12) United States Patent
Fair et al.

(10) Patent No.: US 8,592,376 B2
(45) Date of Patent: Nov. 26, 2013

(54) HAIR CARE COMPOSITIONS

(75) Inventors: Michael J. Fair, Ridgewood, NJ (US); Allwyn Colaco, Morristown, NJ (US); Ashley L. Howell, Oakland, NJ (US)

(73) Assignee: Avon Products, Inc, New York, NY (US)

( * ) Notice: Subject to any disclaimer, the term of this patent is extended or adjusted under 35 U.S.C. 154(b) by 0 days.

(21) Appl. No.: 13/311,685

(22) Filed: Dec. 6, 2011

(65) Prior Publication Data

US 2013/0142750 A1 Jun. 6, 2013

(51) Int. Cl.
*A61K 38/00* (2006.01)

(52) U.S. Cl.
USPC ........................................... 514/20.7

(58) Field of Classification Search
None
See application file for complete search history.

(56) References Cited

U.S. PATENT DOCUMENTS

| | | |
|---|---|---|
| 4,781,917 A | 11/1988 | Luebbe et al. |
| 5,415,857 A * | 5/1995 | Robbins et al. .......... 424/70.122 |
| 5,911,980 A | 6/1999 | Samour et al. |
| 6,254,646 B1 | 7/2001 | Di La Mettrie et al. |
| 6,264,933 B1 | 7/2001 | Bodelin et al. |
| 6,464,969 B2 | 10/2002 | De La Poterie et al. |
| 6,683,126 B2 | 1/2004 | Keller et al. |
| 6,685,952 B1 | 2/2004 | Ma et al. |
| 7,037,515 B2 | 5/2006 | Kalafsky et al. |
| 7,150,878 B2 | 12/2006 | Gonzalez et al. |
| 7,393,365 B2 * | 7/2008 | Bureiko et al. ................... 8/101 |
| 7,393,465 B2 * | 7/2008 | Niesten et al. ........... 252/182.25 |
| 2002/0058776 A1 | 5/2002 | Fost et al. |
| 2003/0121109 A1 | 7/2003 | Devin-Baudoin et al. |
| 2003/0147841 A1 | 8/2003 | Legrand et al. |
| 2003/0206879 A1 | 11/2003 | Glenn et al. |
| 2003/0224954 A1 * | 12/2003 | Wells et al. ................... 510/119 |
| 2007/0041929 A1 | 2/2007 | Torgerson et al. |
| 2007/0154441 A1 | 7/2007 | Gawtrey et al. |
| 2007/0202065 A1 | 8/2007 | Devin-Baudoin et al. |

* cited by examiner

*Primary Examiner* — Anand Desai
*Assistant Examiner* — Melissa Mercier
(74) *Attorney, Agent, or Firm* — David M. Joyal; Joan M. McGillycuddy; Brian C Remy (57) ABSTRACT

Compositions and methods are disclosed for imparting a long-wearing shine to keratin fibers, including hair. The compositions comprise an aminosilicone polymer having a viscosity from about 800 to about 1,600 mm$^2$/s at 25° C., and a functional group equivalent weight from about 8,000 to about 14,000 g/mol. The compositions comprise an aminosilicone polymer and optionally a shine enhancer. The compositions are useful for imparting a long-wearing shine to hair.

13 Claims, 3 Drawing Sheets

HAIR CARE COMPOSITIONS

FIELD OF INVENTION

The present invention relates to methods and compositions for imparting a long-wearing shine to keratin fibers, in particular hair of the head. More specifically, the invention relates to a hair care composition comprising certain aminosilicone polymers that unexpectedly impart a long-wearing shine to hair, without substantially sacrificing other aesthetic properties of the hair.

BACKGROUND OF INVENTION

Organopolysiloxanes have been used to impart smoothness, softness and shine on hair. In particular, amine-modified silicones have been used in hair care products and are substantive to the hair fiber. Traditionally used aminosilicone polymers for hair care products bind electrostatically to keratin fibers and can be very difficult to remove. Because of their strong affinity to hair, there can be considerable build up of aminosilicone polymers on hair over time, which results in an adverse effect to the look and feel of the hair, e.g., tacky feel, matte appearance, etc. Therefore, use of aminosilicone polymers in hair care products are limited to low concentrations so that the look and feel of the hair is not substantially sacrificed due to build-up of aminosilicones on the hair.

It is therefore an object of the invention to provide an aesthetically pleasing composition for application to keratin fibers, such as hair, which enhances the shine. It is a further object of the invention to provide methods for enhancing shine of hair without adversely affecting other aesthetic properties (e.g., appearance, feel, volume, softness, etc.) of the hair.

SUMMARY OF THE INVENTION

In accordance with the foregoing objectives and others, the present invention provides methods and compositions for imparting an improved shine on the hair over time as compared to an otherwise identical composition in the absence of said aminosilicone polymers.

In one aspect of the invention, a method is provided for imparting a long-wearing shine to hair. The method comprises applying to the hair a composition having an aminosilicone polymer having a viscosity from about 800 to about 1,600 mm$^2$/s at 25° C., and a functional group equivalent weight from about 8,000 to about 14,000 g/mol, and optionally a shine enhancer. In a preferred embodiment, the weight ratio of aminosilicone to shine enhancer is from about 1:2 to about 2:1. The composition may be substantially anhydrous.

The presence of the aminosilicone in the composition improves retention of shine on the hair over time as compared to an otherwise identical composition in the absence of the aminosilicone. Preferably, the aminosilicone has a viscosity from about 1,000 to about 1,400 mm$^2$/s at 25° C. Moreover, the aminosilicone may preferably have a functional group equivalent weight (FGEW) from about 10,000 to about 12,000 g/mol. In a preferred embodiment, the aminosilicone has a refractive index greater than 1.4 at 25° C.

The shine enhancer may preferably be an aryl-silicone having a refractive index greater than 1.4 at 25° C., or a hemi-spherical methyl methacrylate crosspolymer. More preferably, the shine enhancer is a phenyltrimethicone or dimethicone.

In certain embodiments, the composition may further include a film former.

In one preferred exemplary embodiment, a hair care composition is provided. The hair care composition includes: (a) from about 1 to about 25 percent by weight of an aminosilicone polymer having a viscosity from about 800 to about 1,600 mm$^2$/s at 25° C., and a functional group equivalent weight from about 8,000 to about 14,000 g/mol, and (b) a substantially anhydrous vehicle. The aminosilicone polymer has a viscosity from about 800 to about 1,600 mm$^2$/s at 25° C., and a functional group equivalent weight from about 8,000 to about 14,000 g/mol. In certain embodiments, the composition may further include a shine enhancer.

These and other aspects of the present invention will become apparent to those skilled in the art after a reading of the following detailed description of the invention, including the illustrative embodiments and examples.

DETAILED DESCRIPTION

In the following description of the invention, it is to be understood that the terms used herein have their ordinary and accustomed meanings in the art, unless otherwise specified. All weights percentages referred to herein are given in terms of "% by weight" of the total composition, unless otherwise indicated.

Unless otherwise provided, the term "alkyl" is intended to embrace straight-chained, branched, or cyclic hydrocarbons, particularly those having from one to 20 carbon atoms, and more particularly $C_{1-2}$ hydrocarbons.

The compositions of the present invention can include, comprise, consist essentially of, or consist of the components of the present invention as well as other ingredients described herein. As used herein, "consisting essentially of" means that the composition or component may include additional ingredients, but only if the additional ingredients do not materially alter the basic and novel characteristics of the claimed compositions or methods as herein set forth.

As used herein, the term "keratin fiber" includes hair of the scalp, eyelashes, eyebrows, facial hair, and body hair such as hair of the arms, legs, etc. Keratin fibers are not limited to humans and also include any keratin fibers from a mammal, such as, for example, pet hair and mammalian fur. The present invention also may be applicable to other fibers such as synthetic fibers.

As used herein, the term "functional group equivalent weight", or FGEW means the ratio of number-average molecular weight (NAVG MW) to the number of functional groups in the polymer.

The present invention is founded, in part, on the discovery that the addition of certain aminosilicones having a combination of a specific range of functional weight equivalent groups (FWEGs), where a high value reflects low number of amino groups in the aminosilicone, and a specific range of viscosity, to a hair care composition imparts and/or retains a long-lasting shine to the hair, particularly when used in combination with a shine enhancer. The compositions of the present invention have been found to impart shine to keratinous fibers, preferably hair, for a longer period of time as compared to an otherwise identical composition in the absence of the aminosilicone. Moreover, the compositions of the present invention may impart wash-resistant aesthetic benefits to the hair, particularly after repeated shampooing, including shine, softness, manageability, and/or reduced flyaway hair, without a materially adverse effect on other aesthetic properties (e.g., appearance, feel, volume, etc.) of the hair. Contrary to aminosilicones traditionally used in hair care products, it has been surprisingly found that compositions of the present invention containing aminosilicones having a combination of certain FWEG and viscosity values can remain on the hair for several washes and do not substantially build-up on the hair after repeated usage such that the look and feel of the hair would be substantially sacrificed. With respect to the look and feel of the hair, by substantially sacrificed or substantial adverse effect, it is meant that the adverse effect to the look and feel of the hair can be readily observed by tactile touch or visual inspection by a human.

Without wishing to be bound by any theory, it is believed that by balancing the amino functionality to the silicone functionality in the aminosilicone, high concentrations of the aminosilicone can be incorporated into products to impart significant wash-resistant and aesthetic benefits, without undesirable build-up and sacrifice to the look and feel of the hair. It is also believed that the compositions of the present invention achieve long-lasting shine not seen with other aminosilicones or with an otherwise identical composition lacking the aminosilicones described herein. Particularly, when used in combination with a shine enhancer, it is believed that the aminosilicone described herein and shine enhancer may form a durable network on the hair that protects the shine enhancer from transfer, water and/or shampoo, and improves retention of shine enhancer on the hair. It is believed that the combination of the aminosilicone described herein and shine enhancer may provide an additive or synergistic aesthetic benefit, in particular long-lasting shine, to the hair, without substantial adverse effects on other aesthetic properties of the hair.

A first component of the hair care compositions of the invention comprises an aminosilicone, having at least one amino group. Generally, an aminosilicone polymer will have a siloxane backbone and will be formed from the polymerization of (i) monomers of the form —O—Si—(R)$_2$—O—, where R is independently selected at each occurrence from lower alkyl groups, but is typically a methyl group at each occurrence, and (ii) monomers of the form —O—Si—(R)(R*)—O—, where R is a lower alkyl group, typically a methyl group, and R* is an amine-substituted alkyl group of the form —(CH$_2$)$_{0-6}$-L-(CH$_2$)$_{1-6}$—NR$_2$, where L is either a bond (i.e., L is absent) or a group of the form —NR$^N$—, where R$^N$ is independently selected at each occurrence from hydrogen or lower alkyl, most typically hydrogen. In specific embodiments, the R* is either a group —(CH$_2$)$_{1-6}$—NH$_2$ or a group —(CH$_2$)$_{1-6}$—NH—(CH$_2$)$_{1-6}$—NH$_2$, or more typically a group —(CH$_2$)$_{2-4}$—NH$_2$ or a group —(CH$_2$)$_{2-4}$—NH—(CH$_2$)$_{1-3}$—NH$_2$. The ratio of siloxane monomer unit (i) to amino-functionalized siloxane monomer unit (ii) in the polymer will be selected such that the functional group equivalent weight (FGEW) is from about 8,000 to about 14,000 g/mol, and the overall molecular weight of the polymer is such that the viscosity is from about 800 to about 1,600 mm$^2$/s (25° C.).

(I)

where
x is an integer from 0 to 6, preferably from 1 to 6, more preferably from 2 to 4, and most preferably 3;
y is an integer from 1 to 6, preferably from 1 to 3, and more preferably 2; and
m and n are independently each an integer from 1 to 5,000 and are selected to provide a FGEW from about 8,000 to about 14,000.

In particular, m and n are integers selected such that the FGEW is from about 8,000 to about 14,000 g/mol and the viscosity is from about 800 to about 1,600 mm$^2$/s (25° C.). Preferably, the FGEW of the aminosilicone is from about 10,000 to about 12,000 g/mol. More preferably, the FGEW of the aminosilicone is about 11,000 g/mol. Also preferred are aminosilicones having a viscosity from about from about 1,000 to about 1,400 mm$^2$/s (25° C.). More preferably, the viscosity of the aminosilicone is about 1,200 mm$^2$/s.

In certain exemplary embodiments, the aminosilicone imparts a good gloss or shine to the hair. In particular, the aminosilicone may have a refractive index greater than 1.4 at 25° C. Preferably, the aminosilicone may have a refractive index from about 1.401 to about 1.5 at 25° C., including embodiments wherein the refractive index is 1.402, 1.403, 1.404, 1.405, 1.425, 1.45 or 1.475 at 25° C.

Additionally, the aminosilicone may have a specific gravity less than 1 at 25° C. Preferably, the aminosilicone may have a specific gravity less than 0.99 at 25° C. More preferably, the aminosilicone may have a specific gravity from about 0.95 to about 0.99 at 25° C., including embodiments wherein the specific gravity is 0.96, 0.97 or 0.98 at 25° C.

One particularly preferred aminosilicone polymer is available from Shin-Etsu Chemical Co., Ltd. under the trade name KF-8005. The KF-8005 material has a FGEW of 11,000 g/mol and a viscosity of 1,200 mm$^2$/s (25° C.). In addition, the KF-8005 material has a specific gravity of 0.97 (25° C.) and a refractive index of 1.403 (25° C.).

The aminosilicone polymer is typically present from about 0.01% to about 25% by weight of the total composition. More typically, the aminosilicone polymer will comprise from about 1% to about 25% by weight of the composition. Preferably, the aminosilicone polymer will comprise from about 5% to about 10% by weight of the composition, including embodiments wherein the aminosilicone is present at about 6%, 7%, 8%, or 9% by weight of the composition.

A second component of the hair care compositions of the invention comprises a shine enhancer. It is contemplated that the aminosilicone described above also imparts shine to the hair and that a separate shine enhancer is not necessary in the composition of the present invention. Thus, in some embodiments, the composition will be free of shine enhancers. In another embodiment, the composition includes a shine enhancer.

In some embodiments, the shine enhancer is, without limitation, an aryl-silicone having a high refractive index or a hemi-spherical methyl methacrylate crosspolymer. In general, any aryl-substituted silicone having a refractive index of greater than 1.4 at 25° C. is contemplated to be suitable for imparting shine to the hair. Particular mention may be made of phenyltrimethicone, which is available under the trade names SI-TEC PTM 1000 (ISP) and PDM20 (Wacker-Belsii). The PDM20 material has a refractive index of 1,437 at 25° C. Also suitable as a shine enhancer is Trimethylsiloxyphenyl Dimethicone (INCI name), which is available under the trade name PDM 1000 (Wacker-Belsil). The PDM 1000 material has a refractory index of 1.461 at 25° C. Another suitable silicone fluid is trimethylsiloxyphenyl dimethicone. Phenyl silicones such as pentaphenyl trimethyl trisiloxane or tetraphenyl tetramethyl trisiloxane, commercially available as HRI fluids from Dow Corning HRI, are also useful for enhancing shine. Certain organic compounds, such as octyl methoxy cinnamate, may also be used to enhance shine. Particularly preferred as a shine enhancer is dimethicone, such as SI-TEC™ DM 500000 (ISP).

Lens-shaped particles such as hemi-spherical PMMA are also useful for imparting shine. One such commercially available material is a hemi-spherical methyl methacrylate crosspolymer sold under the trade name 3D Tech PW (Plain) XP (Kobo). Other suitable shine enhancers include phenylpropyldimethylsiloxysilicate, polybutene, polyisobutene, and hydrogenated polyisobutene.

The shine enhancer is typically present from about 0.01% to about 50% by weight of the total composition. More typically, the shine enhancer will comprise from about 1% to about 50% by weight of the composition. Preferably, the shine enhancer will comprise from about 1% to about 25% by weight of the composition. Most preferably, the shine enhancer is from about 3% to about 6% by weight of the composition.

In certain exemplary embodiments, the aminosilicone and the shine enhancer may be present in weight ratios from about 10:1 to about 1:10, or from about 5:1 to about 1:5, or from about 2:1 to about 1:2, or about 1:1.

A separate film former is not necessary in the composition of the present invention. Thus, in some embodiments, the compositions will be free of film formers, such as polymeric film formers, waxes, oils, etc., or will be substantially free of film formers, by which is meant that the composition will comprise less than about 1% by weight film former, and preferably less than about 0.5% by weight film former, and more preferred still, less than about 0.1% by weight.

In other embodiments, a film-former may be included in the compositions. The film former preferably comprises a hydrophobic material. The hydrophobic film former may be any hydrophobic film former suitable for use in a cosmetic composition including, but not limited to, hydrophobic film-forming polymers. The term film-forming polymer may be understood to indicate a polymer which is capable, by itself or in the presence of at least one auxiliary film-forming agent, of forming a continuous film which adheres to a surface and functions as a binder for the particulate material. The term "hydrophobic" film-forming polymer will typically refer to a polymer with a solubility in water at 25° C. of less than about 1% by weight or one in which the monomeric units of the polymer individually have a solubility in water of less than about 1% by weight at 25° C. Alternatively, a "hydrophobic" film forming polymer may be said to be one which partitions predominantly into the octanol phase when shaken with a mixture of equal volumes of water and octanol. By predominately is meant more the 50% by weight, but preferably more than 75% by weight, more preferably more than 95% by weight will partition into the octanol phase.

The film formers can be either natural or synthetic, polymeric or non-polymeric, resins, binders, with low or high molar mass. Polymeric film formers can be either natural or synthetic, addition or condensation, homochain or heterochain, monodispersed or polydispersed, organic or inorganic, homopolymers or copolymers, linear or branched or crosslinked, charged or uncharged, thermoplastic or thermoset, elastomeric, crystalline or amorphous or both, isotactic or syndiotactic or atactic.

Polymeric film formers include polyolefins, polyvinyls, polyacrylates, poly-urethanes, silicones, polyamides, polyesters, fluoropolymers, polyethers, polyacetates, polycarbonates, polyimides, rubbers, epoxies, formaldehyde resins, and homopolymers and copolymers of the foregoing.

Suitable hydrophobic (lipophilic) film-forming polymers include, without limitation, those described in U.S. Pat. No. 7,037,515 to Kalafsky, et al.; U.S. Pat. No. 6,685,952 to Ma et al.; U.S. Pat. No. 6,464,969 to De La Poterie, et al.; U.S. Pat. No. 6,264,933 to Bodelin, et al.; U.S. Pat. No. 6,683,126 to Keller et al.; and U.S. Pat. No. 5,911,980 to Samour, et al., the disclosures of which are hereby incorporated by reference.

Copolymers comprising one or more blocks selected from styrene (S), alkylstyrene (AS), ethylene/butylene (EB), ethylene/propylene (EP), butadiene (B), isoprene (I), acrylate (A) and methacrylate (MA), or a combination thereof, are contemplated to be suitable hydrophobic film formers. Particular mention is made of Ethylene/Propylene/Styrene and Butylene/Ethylene/Styrene copolymer including those sold under the trade name Versagel MD 1600 from Penreco as Gellants in IDD.

Special mention may be made of polyalkylenes, and in particular $C_2$-$C_{20}$ alkene copolymers, such as polybutene; alkylcelluloses with a linear or branched, saturated or unsaturated $C_1$-$C_8$ alkyl radical, such as ethylcellulose and propylcellulose; copolymers of vinylpyrrolidone (VP) and in particular copolymers of vinylpyrrolidone and of $C_2$ to $C_{40}$ and better still $C_3$ to $C_{20}$ alkene, including the copolymers of vinyl pyrollidone with eicosene or dodecane monomers sold under the tradenames Ganex V 220 and Ganex V 216 Polymers (ISP Inc. of Wayne, N.J.); silicone polymers and polyorganosiloxanes, including, without limitation, polyalkyl siloxane, polyaryl siloxane, or a polyalkylaryl siloxane, with special mention being made of polydimethylsiloxanes; polyanhydride resins such as those available from Chevron under the trade name PA-18; copolymers derived from maleic anhydride and $C_3$ to $C_{40}$ alkenes such as octadecene-1; polyurethane polymers, such as Performa V 825 (New Phase Technologies) and those disclosed in U.S. Pat. No. 7,150,878 to Gonzalez, et al., incorporated by reference herein; and polymers and copolymers made from esters of vinylic acid monomers, including, without limitation, (meth)acrylic acid esters (also referred to as (meth)acrylates), for example, alkyl(meth)acrylates, wherein the alkyl group is chosen from linear, branched and cyclic ($C_1$-$C_{30}$) alkyls, such as, for example, ($C_1$-$C_{20}$)alkyl (meth)acrylates, and further still ($C_6$-$C_{10}$)alkyl(meth)acrylates. Among the alkyl(meth)acrylates which may be mentioned are those chosen from methyl methacrylate, ethyl methacrylate, butyl methacrylate, isobutyl methacrylate, 2-ethylhexyl methacrylate, lauryl methacrylate, and the like. Among the aryl(meth)acrylates which may be mentioned are those chosen from benzyl acrylates, phenyl acrylate, and the like. The alkyl group of the foregoing esters may be chosen, for example, from fluorinated and perfluorinated alkyl groups, that is to say that some or all of the hydrogen atoms of the alkyl group are replaced with fluorine atoms. Mention may also be made of amides of the acid monomers such as (meth)acrylamides, for example, N-alkyl(meth)acrylamides, such as ($C_1$-$C_{20}$) alkyls, including without limitation, N-ethylacrylamide, N-t-butylacrylamide, N-t-octylacrylamide and N-undecylacrylamide. Vinyl polymers for the hydrophobic film-forming polymer may also result from the homopolymerization or copolymerization of at least one monomer chosen from vinyl esters, olefins (including fluoroolefins), vinyl ethers, and styrene monomers. For example, these monomers may be copolymerized with at least one of acid monomers, esters thereof, and amides thereof, such as those mentioned above. Non-limiting examples of vinyl esters which may be mentioned are chosen from vinyl acetate, vinyl neodecanoate, vinyl pivalate, vinyl benzoate and vinyl t-butylbenzoate. Among the olefins which may be mentioned are those chosen, for example, from ethylene, propylene, butene, isobutene, octene, octadecene, and polyfluorinated olefins chosen, for example, from tetrafluoroethylene, vinylidene fluoride, hexafluoropropene and chlorotrifluoroethylene. Styrene monomers which may be mentioned are chosen, for example, from styrene and alpha-methylstyrene. The list of monomers given is not limiting, and it is possible to use any monomer known to those skilled in the art which falls within the categories of acrylic and vinyl monomers (including monomers modified with a silicone chain) which result in hydrophobic films. In this regard, particular mention may be made of the commercially available film formers cyclopentasiloxane (and) Acrylates/Dimethicone Copolmer (KP-545, Shin-Etsu Chemical Co., Ltd).

Other film formers known in the art can be used advantageously in the composition. These include acrylate copolymers, acrylates $C_{12-22}$ alkyl methacrylate copolymer, acrylate/octylacrylamide copolymers, acrylate/VA copolymer, amodimethicone, AMP/acrylate copolymers, behenyl/isostearyl, butylated PVP, butyl ester of PVM/MA copolymers, calcium/sodium PVM/MA copolymers, dimethicone, dimethicone copolymers, dimethicone/mercaptopropyl methicone copolymer, dimethicone propylethylenediamine behenate, dimethicolnol ethylcellulose, ethylene/acrylic acid copolymer, ethylene/MA copolymer, ethylene/VA copolymer, fluoro $C_{2-8}$ alkyldimethicone, $C_{30-38}$ olefin/isopropyl maleate/MA copolymer, hydrogenated styrene/butadiene copolymer, hydroxyethyl ethylcellulose, isobutylene/MA copolymer, methyl methacrylate crosspolymer, methylacryloyl ethyl betaine/acrylates copolymer, octadecene/MA copolymer, octadecene/maleic anhydride copolymer, octylacrylamide/acrylate/butylaminoethyl methacrylate copolymer, oxidized polyethylene, perfluoropolymethylisopropyl ether, polyethylene, polymethyl methacrylate, polypropylene, PVM/MA decadiene crosspolymer, PVM/MA copolymer, PVP, PVP/decene copolymer, PVP/eicosene copolymer, PVP/hexadecene copolymer, PVP/MA copolymer, PVP/VA copolymer, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tetramethyl tetraphenyl trisiloxane, tricontanyl PVP, trimethyl pentaphenyl trisiloxane, trimethylsiloxysilicate, VA/crotonates copolymer, VA/crotonates/vinyl proprionate copolymer, VA/butyl maleate/isobornyl acrylate copolymer, vinyl caprolactam/PVP/dimethylaminoethyl methacrylate copolymer, and vinyldimethicone.

Additional non-limiting representatives of hydrophobic film-forming polymers include at least one polycondensate chosen from polyurethanes, polyurethane-acrylics, polyurethane-polyvinylpyrrolidones, polyester-polyurethanes, polyether-polyurethanes, polyureas and polyurea/polyurethanes. The polyurethanes may be for example, at least one chosen from aliphatic, cycloaliphatic, and aromatic polyurethanes, polyurealurethanes, and polyurea copolymers comprising at least one of: at least one sequence of at least one aliphatic polyester origin, cycloaliphatic polyester origin, and aromatic polyester origin at least one branched and unbranched silicone sequence, for example, from polydimethylsiloxane and polymethylphenylsiloxane, and at least one sequence comprising fluorinated groups. Additional non-limiting representatives of polycondensates may be chosen from polyesters, polyesteramides, fatty-chain polyesters, polyamides resins, epoxyester resins, arylsulphonamide-epoxy resins, and resins resulting from the condensation of formaldehyde with an arylsulphonamide.

The hydrophobic film may also be formed in situ by employing a resin which cures after application to the hair, including for example, a polydimethylsiloxane film formed by in situ hydrosilation of a hydrosilane and an olefinic-substituted siloxane or by in situ polycondensation of alkoxy-functionalized siloxanes.

Preferred polymeric film formers include acrylates, alkyl acrylates, polyurethanes, fluoropolymers such as Fluomer (polyperfluoroperhydrophenanthrene) and silicone polymers. Particularly preferred are silicone acrylates such as acrylates/dimethicone copolymers sold under the trade names KP-545 or KP-550 (Shin-Etsu).

Other film formers that may be employed include, without limitation, natural, mineral and/or synthetic waxes. Natural waxes are those of animal origin, including without limitation beeswax, spermaceti, lanolin, and shellac wax, and those of vegetable origin, including without limitation carnauba, candelilla, bayberry, and sugarcane wax, and the like. Mineral waxes contemplated to be useful include, without limitation ozokerite, ceresin, montan, paraffin, microcrystalline, petroleum, and petrolatum waxes. Synthetic waxes include, for example, Fischer Tropsch (FT) waxes and polyolefin waxes, such as ethylene homopolymers; ethylene-propylene copolymers, and ethylene-hexene copolymers. Representative ethylene homopolymer waxes are commercially available under the tradename POLYWAX®. Polyethylene (Baker Hughes Incorporated). Commercially available ethylene-α-olefin copolymer waxes include those sold under the tradename PETROLITE®. Copolymers (Baker Hughes Incorporated). Another wax that is suitable is dimethiconol beeswax available from Noveon as ULTRABEE® dimethiconol ester.

Combinations of any of the foregoing film formers are also contemplated to be suitable, including combinations or polymeric and non-polymeric film formers.

Various fillers and additional components may be added. Suitable fillers include without limitation silica, treated silica, talc, zinc stearate, mica, kaolin, Nylon powders such as ORGASOL™, polyethylene powder, TEFLON™, boron nitride, copolymer microspheres such as EXPANCEL™ (Nobel Industries), POLYTRAP™ (Dow Coring) and silicone resin microbeads (TOSPEARL™ from Toshiba), and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, polymethylmethacrylate powder (PMMA), copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide; and stabilizers/rheology modifiers, for example, Bentone Gel and Rheopearl TT2. Other useful powders are disclosed in U.S. Pat. No. 5,688,831, the disclosure of which is hereby incorporated by reference.

The aggregate amount of all such additional pigments, colorants, and fillers is not particularly restricted provided that the shine of the hair is not compromised. Typically, all additional pigments, colorants, fillers, etc., if present, will collectively comprise from about 0.1% to about 5% of the total composition, but more typically will comprise from about 0.1% to about 2% by weight of the composition.

In addition, the compositions of the invention may optionally comprise other active and inactive ingredients typically associated with cosmetic and personal care products selected from the group consisting of emulsifying agents, antioxidants, surfactants, chelating agents; gelling agents, thickeners, emollients, humectants, moisturizers, vitamins, minerals, viscosity and/or rheology modifiers, sunscreens, alpha-hydroxy acids, alpha-keto acids, anti-mycobacterial agents, antifungal agents, antimicrobials, anti-inflammatory agents, anti-irritants, insect repellents, skin cooling compounds, skin protectants, lubricants, fragrances, depigmenting agents, hypopigmenting agents, preservatives, stabilizers, photostabilizing agents, and mixtures thereof. Collectively, all such additional components suitably will comprise less than 5% by weight of the composition, but will typically comprise less than about 2% by weight, and will preferably will comprise less than 1% by weight, more preferably less than 0.5% by weight, and ideally less than 0.1% by weight of the total composition.

The inventive hair care compositions will comprise a cosmetically acceptable vehicle. By "cosmetically acceptable" is meant that the vehicle is safe for contact with a human integument. The vehicle may comprise a liquid, comprising a single phase, a dual-phase system, or an emulsion. Emulsions include oil-in-water, silicone-in-water, water-in-oil, water-in-silicone, and the like. Where the product is intended as a spray, it may be desirable to employ a single phase vehicle, or a dual phase vehicle comprising an aqueous phase and an oil phase, the oil phase comprising a silicone oil. When formulated as an emulsion, an emulsifier is typically included. In other embodiments, the composition is substantially free or free of an emulsifier. By substantially free of an emulsifier is meant that no emulsifier is deliberately added to the composition and the amounts present, if any, are so low as to not have a measurable impact on the stability of an emulsion. However, it is contemplated that any cosmetically acceptable vehicle known in the art will be useful.

The hair care compositions of the invention can be, but are not necessarily, provided as anhydrous or substantially anhydrous formulations. By "substantially anhydrous" is mean that the weight percentage of water in the composition is less than about 1%, preferably less than 0.5%, and most preferably less than about 0.1% by weight. Typically, the anhydrous compositions are substantially free of water by which is meant that water is not deliberately added to the compositions and the level of water is no more than would be expected based on the absorption of water from the air.

In one embodiment, the vehicle may comprise a volatile solvent. Typically, a volatile solvent may have a vapor pressure of above about 0.01 mmHg at 20° C. Volatile solvents may include volatile $C_{5-12}$ hydrocarbons, aromatic hydrocarbons (e.g., xylenes, toluene, etc.), ketones (e.g., acetone, methylethyl ketone, etc.), ethers (e.g., diethyl ether, methylethyl ether, etc.), perfluorohydrocarbons, hydrofluoroethers, freons, volatile silicones, lower alcohols, esters of acetic acid (e.g., ethylacetate, butylacetate, etc.) and the like. Preferred volatile solvents will be cosmetically acceptable, by which is meant that they are safe and non-irritating when applied to the body under conditions of normal use.

Volatile silicones are a preferred volatile solvent. By volatile silicone is meant that the oil readily evaporates at ambient temperatures. Typically, volatile silicone oils will exhibit a vapor pressure ranging from about 1 Pa to about 2 kPa at 25° C.; will preferably have a viscosity of from about 0.1 to about 10 centistokes, preferably about 5 centistokes or less, more preferably about 2 centistokes or less, at 25° C.; and will boil at atmospheric pressure at from about 35° C. to about 25° C. Volatile silicones include cyclic and linear volatile dimethylsiloxane silicones, including 0.5 cst dimethicone, 0.65 cst dimethicone, 1 cst dimethicone, and 1.5 cst dimethicone. In one embodiment, the volatile silicones may include cyclodimethicones, including tetramer (D4), pentamer (D5), and hexamer (D6) cyclomethicones, or mixtures thereof. Suitable dimethicones are available from Dow Corning under the name DOW CORNING 200® Fluid and have viscosities ranging from 0.65 to 5 centistokes. Suitable non-polar, volatile liquid silicone oils are disclosed in U.S. Pat. No. 4,781,917, herein incorporated by reference in its entirety. Additional volatile silicone materials are described in Todd et al., "Volatile Silicone Fluids for Cosmetics," *Cosmetics and Toiletries*, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345 (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as methyltrimethicone, trisiloxane, hexamethyldisiloxane, octamethyltrisiloxane, decamethyltetrasiloxane, and dodecamethylpentasiloxane to name a few.

Lower ($C_1$ to $C_6$) alcohol solvents, including methanol, ethanol, propanol, and isopropanol, are also contemplated to be useful. Ethanol is particularly preferred due to its high volatility and low toxicity. Preferably, the ethanol is anhydrous ethanol, such as SD Alcohol 40 from Exxon.

Among the volatile $C_{5-12}$ hydrocarbons, special mention may be made of isododecane which is available under the trade name Permethyl-99A (Presperse Inc.). Suitable fluorinated solvents include, without limitation, perfluoroethers, perfluorodecalin, perfluoromethyldecalin, perfluorohexane, perfluoromethylcyclohexane, perfluorodimethylcyclohexane, perfluoroheptane, perfluorooctane, perfluorononane, and perfluoromethyl cyclopentane, for example.

In a preferred embodiment, the solvent will comprise a combination of a volatile silicone, preferably cyclomethicone pentamer, and anhydrous ethanol. Preferably, the volatile silicone (cyclomethicone pentamer) will comprise from about 1% to about 99% and the ethanol will comprise from about 1% to about 99% by weight of the solvent system. More particularly, the volatile silicone (cyclomethicone pentamer) will comprise from about 50% to about 99% and the ethanol will comprise from about 1% to about 50% by weight of the solvent system. In a preferred embodiment, volatile silicone (cyclomethicone pentamer) will comprise from about 70% to about 90% and ethanol will comprise from about 10% to about 30% by weight of the solvent system.

In a further embodiment, the compositions according to the invention will comprise ethanol, preferably anhydrous, in combination with one or more solvents having a vapor pressure at 25° C. which is less than the vapor pressure of ethanol. In another embodiment, the compositions according to the invention will comprise ethanol, preferably anhydrous, in combination with one or more solvents having a vapor pressure at 25° C. which is greater than the vapor pressure of ethanol.

The compositions may be in any suitable form, including but not limited to gels, creams, liquids, emulsions, sprays, and the like. The vehicle may comprise a single phase, a dual-phase system, or an emulsion. Emulsions include oil-in-water, silicone-in-water, water-in-oil, water-in-silicone, and the like. When formulated as an emulsion, an emulsifier is typically included. The composition of the present invention may be any suitable hair care composition, including shampoo, conditioner, styling products (e.g., gel, mousse, etc.), amongst others.

The inventive composition may be applied, preferably sprayed, onto dry hair or wet hair (hair of the body, scalp, beard, mustache, eyelashes, etc.) to impart a long-wearing shine. Thus, for example, the composition may be applied to the hair while it is dry, when it is only minimally wet, or after submersion in water. Typically, the composition may be applied to hair before shampooing of the hair. Alternatively, the composition may be applied to the hair following shampooing of the hair. The composition may also be applied during shampooing of the hair. In addition, the hair care composition can be re-applied at any time, as the consumer desires. In one embodiment, the hair care composition may be re-applied to the hair before every wash. The compositions are beneficially applied after each shampooing, but resist one, two, three, four, six, eight, ten or even more shampooings before reapplication is required. The foregoing may be tested using hair swatches treated with the inventive compositions.

EXAMPLE I

The aesthetic effect of an aminosilicone having a viscosity from about 800 to about 1,600 mm$^2$/s at 25° C., and a functional group equivalent weight from about 8,000 to about 14,000 g/mol was investigated in relation to the retention of shine of hair treated with the hair care composition. Compositions were prepared according to Table 1.

TABLE 1

| Components | Sample Number: 1 Weight % | 2 | 3 |
|---|---|---|---|
| Aminosilicone (Shin-Etsu KF-8002) | 10 | — | — |
| Aminosilicone (Shin-Etsu KF-8004) | — | 10 | — |
| Aminosilicone (Shin-Etsu KF-8005) | — | — | 10 |
| Dimethicone (SI-TEC ™ DM 500000) | 5 | 5 | 5 |
| Cyclopentasiloxane (Shin-Etsu KF-995) | 35 | 35 | 35 |
| Cyclohexasiloxane (and) Cyclopentasiloxane (Xiameter PMX-0345 cyclosiloxane blend) | 20 | 20 | 20 |
| Silicone Fluid (Shin-Etsu X-21-5847) | 30 | 30 | 30 |
| Total: | 100 | 100 | 100 |

Samples 1 and 2 include aminosilicones having low FGEWs, which are indicative of aminosilicones having high amine contents (i.e., having more amino groups as compared to an aminosilicone having a higher FGEW). Specifically, Sample 1 includes an aminosilicone available from Shin-Etsu Chemical Co., Ltd. under the trade name KF-8002. The KF-8002 material has a FGEW of 1,700 g/mol, a viscosity of 1,100 mm$^2$/s (25° C.), a specific gravity of 0.98 (25° C.) and a refractive index of 1.408 (25° C.). Sample 2 includes an aminosilicone also available from Shin-Etsu Chemical Co., Ltd. under the trade name KF-8004. The KF-8004 material has a FGEW of 1,500 g/mol, a viscosity of 800 mm$^2$/s (25° C.), a specific gravity of 0.98 (25° C.) and a refractive index of 1.408 (25° C.). In contrast, Sample 3 includes aminosilicones having a high FGEW, which is indicative of an aminosilicone having a low amine content, or fewer amino groups as compared to an aminosilicone having a lower FGEW. Sample 3 includes an aminosilicone available from Shin-Etsu Chemical Co., Ltd. under the trade name KF-8005. The KF-8005 materials has a FGEW of 11,000 g/mol, a viscosity of 1,200 mm$^2$/s (25° C.), a specific gravity of 0.97 (25° C.) and a refractive index of 1.403 (25° C.).

Each hair care composition was prepared by adding each ingredient, one at a time, to a container, and mixing the mixture therein for five (5) minutes between additions of each component. After all of the ingredients or a sample hair care composition have been added to the vessel, the mixture is further mixed for another twenty (20) minutes or until the mixture appears to be uniform (e.g., substantially homogenous).

The shine retention of hair treated with Samples 1 through 3 were examined using the instrument and testing protocol described below.

Bossa Nova Shine Measurements

The instrument used to measure the shine of each of the hair samples is a Bossa Nova. Instrument. Instrument results are based on the principle of using polarized illumination with a polarizing camera that is able to separate polarized light that is reflected from a surface (specular) and unpolarized light that scatters (diffuse light). The more specular light, the more shine on hair.

The method to measure shine is based on image analysis. The visual impression of shine is largely due to two mechanisms, i.e., reflection and diffusion of light. Hair reflects incoming light like a mirror and can also diffuse it. The reflection mechanism preserves incoming polarization (parallel polarization) and diffusion creates crossed polarization.

Measuring both amounts of light allows the quantification of shine by software and patented camera design.

The imaging system instrumentation is a technology that allows for the quantitation of shine on hair swatches by quantitating shine in vivo (or on real models in real time), or by visually comparing shine products by gloss mapping. There are two set-up configurations; one to measure hair swatches on a cylinder and the other to measure hair with a special face or lighting.

The shine band is the shiny section of hair focused under the camera lens. Once the hair is positioned on the cylinder, the region of interest was measured by the software. Shine data were obtained by integrating areas under the curves from specular and diffused light. Specifically, the Bossa Nova shine is calculated by the formula: $P/(C \times W)$. P is amount of specular light; C is diffused light (area under curve); and W is width of specular peak.

One of the advantages the image analysis technique described above is that there is no limitation to flat surfaces and shine may be measured "instantly" in real time. An article featured by *Cosmetics and Toiletries Magazine*, "In Vivo Quantitative Evaluation of Gloss," October 2004, features the Bossa Nova instrument and shine methodology. ISP, International Specialty Products, an ingredient manufacturer, has also published work using image analysis technique to quantify shine.

Shine Retention Test Method

Hair samples, light golden brown medium density hair tresses (¾ inch width and 10 inch in length), were obtained from International Hair Importers. Using a pipette, 1.0 g of a hair care composition was placed on to the hair sample and manually distributed evenly from top to bottom. Each hair sample was then blow-dried for three (3) minutes and combed five (5) times.

The Bossa Nova instrument was calibrated using a white photo paper strip in accordance with the instrument manufacturer's instructions. A hair sample was first combed with a large teeth comb ten (10) times. One end of the hair tress was then attached to one side of a sample holder. The hair was then combed five (5) more times and the unattached end of the hair sample was attached to a second side of the sample holder. The holder was then slid into a chamber of the Bossa Nova instrument and the shine of the hair sample was recorded.

After the initial shine measurement, the hair sample was rinsed under running water at a temperature between 100 to 110° F., for 30 seconds. Excess water from the hair sample was manually removed by squeezing the hair sample between the middle and index fingers.

To wash each hair sample, 0.5 mL of a detergent solution having 12% sodium lauryl ether sulfate (SLES)) was to the hair sample using a pipette. The detergent solution was manually distributed throughout the hair sample along the length of the hair sample from top to bottom by repeated downward motions for 30 seconds. The hair sample was then placed under running warm water, at a temperature between 100 to 110° F., and rinsed for 30 seconds. The hair sample is subsequently dried using a blow-dryer and the shine of the sample is measured a second time using the Bossa Nova instrument. The washing and drying steps are repeated until the shine of the hair sample is at or about the shine of untreated hair samples (i.e., baseline shine).

Figure 1:
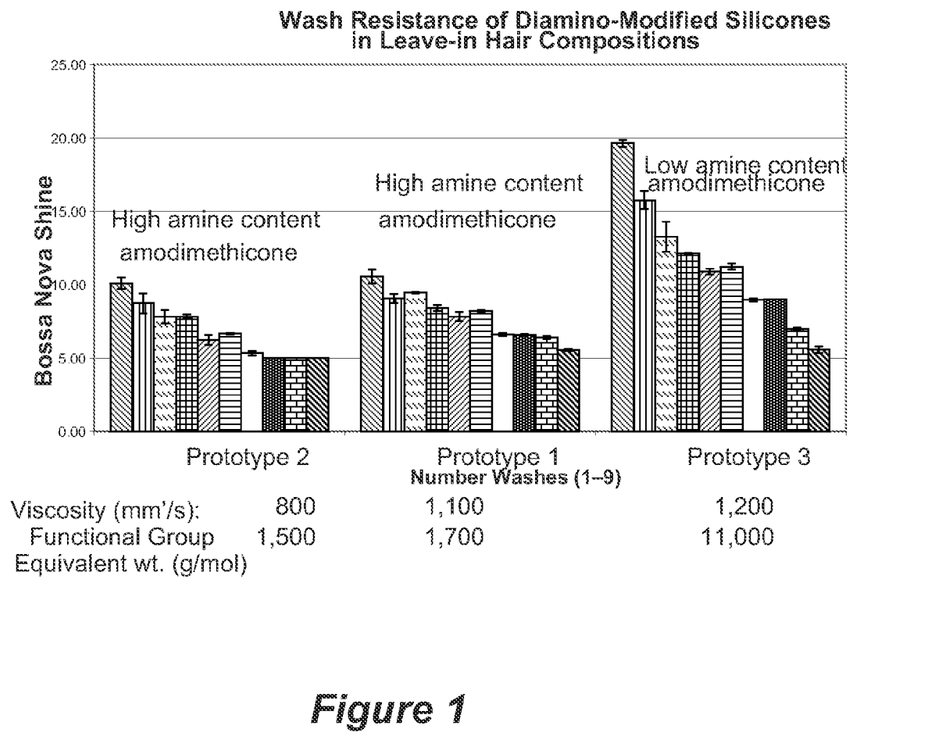
FIG. 1 shows wash resistance of diamino-modified silicones in leave-in hair compositions.

The results of the shine retention test for each of Samples 1 through 3 is shown in FIG. 1. As can be seen from FIG. 1, Sample 3 containing the KF-8005, which has a FGEW of 11,000 g/mol and a viscosity of 1,200 mm$^2$/s (25° C.) provides a higher initial shine as compared to Samples 1 and 2, each of which includes an aminosilicone having a significantly lower FGEW. Furthermore, the data of FIG. 1 shows that Sample 3 is more wash resistant than Samples 1 and 2 because Sample 3 retained enhanced shine after more washes as compared to Samples 1 and 2. Therefore, the results show that an aminosilicone having a FGEW of 11,000 g/mol and a viscosity of 1,200 mm$^2$/s (25° C.) imparts a superior, long-wearing shine to the hair as compared to aminosilicones having significantly lower FGEWs (e.g., less than 8,000 g/mol).

EXAMPLE II

The aesthetic effect of an aminosilicone having a FGEW of 11,000 g/mol and a viscosity of 1,200 mm$^2$/s (25° C.) (e.g., the KF-8005 material) in combination with a cyclopentasiloxane as compared to an aminosilicone having a low FGEW in combination with the same cyclopentasiloxane was investigated in relation to the amount of build-up of silicone on the hair. One composition (Sample 4) was prepared with 10% of the KF-8005 and 90% of cyclopentasiloxane (Xiameter PMX-0245, Dow Corning). Another composition (Sample 5) was prepared with 10% of an aminosilicone having a low FGEW available from Momentive Specialty Chemicals Inc. under the trade name SF1708 and 90% of cyclopentasiloxane (Xiameter PMX-0245, Dow Corning). The SF1708 material is an aminopropylaminoethylpolysiloxane (CAS Reg. No. 71750-79-3), which has a FGEW of 1,250 g/mol and a viscosity of 1250-2500 mm$^2$/s at 25° C.

Each of Samples 4 and 5 were applied onto three different hair samples. For each hair sample, 0.5 gram of hair care composition was applied to every 5 grams of hair (i.e., 10% based on hair weight). The hair care composition was manually distributed throughout the hair sample along the length of the hair sample from top to bottom by repeated down ward motions for about 30 seconds. The hair sample was subsequently dried using a blow-dryer on a high setting for about 2 minutes. The amount of build-up of silicone on the hair sample after initial treatment with the hair care composition was determined using Energy Dispersive X-ray (EDAX). The three hair samples for each hair care composition (i.e., Sample 4 and Sample 5) were blended and analyzed for % relative silicon concentration on the hair surface. EDAX statistics were generated from 17 measurements discarding the highest and lowest result. The shine of the hair samples were also determined using the Bossa Nova shine measurement procedures discussed above for Example I.

To wash each hair sample, 0.5 mL of a detergent solution having 12% sodium lauryl ether sulfate (SLES)) was to the hair sample using a pipette. The detergent solution was manually distributed throughout the hair sample along the length of the hair sample from top to bottom by repeated downward motions for 30 seconds. The hair sample was then placed under running warm water, at a temperature between 100 to 110° F., and rinsed for 30 seconds. The hair sample was subsequently dried using a blow-dryer. The washing and drying steps were repeated an additional five (5) times. The amounts of build-up of silicone on the hair sample after the second and fourth washes were determined using EDAX. The shine of the hair sample was also determined using the Bossa Nova shine measurement procedures.

To study the long-term usage performance and identify any build-up issues, after the hair sample was washed and dried six (6) times, 0.5 gram of hair care composition was applied a second time to every 5 grams of hair (i.e., 10% based on hair weight) in the same manner as described for the initial application. The amount of build-up of silicone on the hair sample after the second treatment with the hair care composition was determined using EDAX. The shine of the hair samples were also determined using the Bossa Nova shine measurement procedures.

The washing and drying steps described above was performed an additional six (6) times. The amounts of build-up of silicone on the hair sample after the second and fourth washes were determined using EDAX. The shine of the hair samples were also determined using the Bossa Nova shine measurement procedures.

A third application of 0.5 gram of hair care composition was applied to every 5 grams of hair (i.e., 10% based on hair weight) in the same manner as described above for the initial application. The amount of build-up of silicone on the hair sample after the second treatment with the hair care composition was determined using EDAX. The shine of the hair samples were also determined using the Bossa Nova shine measurement procedures.

The washing and drying steps described above was performed an additional six (6) times. The amounts of build-up of silicone on the hair sample after the second and fourth washes were determined using EDAX. The shine of the hair samples were also determined using the Bossa Nova shine measurement procedures.

Figure 2:
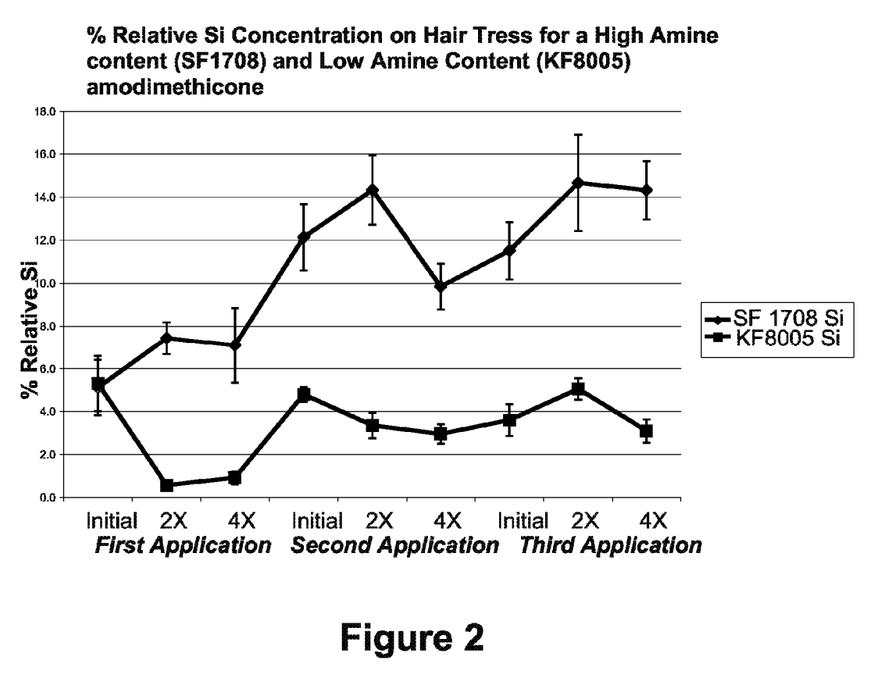
FIG. 2 shows percent relative Si concentration on hair tresses for high amine content and low amine content amodimethicone.

The results of the EDAX build up test for each of Samples 4 and 5 are shown in FIG. 2. As can be seen from FIG. 2, Sample 5, containing the SF1708 material which has a high amine content (a FGEW of 1,250 g/mol), results in a significant increase in the amount of silicon build-up after the second and third application as compared to Sample 4 which contains the low amine content KF-8005 material. Surprisingly, it was observed that the KF-8005 material did not significantly build up on the hair after each successive application. After 4 to 6 washes following the second application of Sample 4, the hair care composition containing the KF-8005 material, the amount of silicon (% Si) remaining was only reduced by about 50%. However, additional treatment of the hair sample with Sample 4 did not result in silicon build up, as it was observed with Sample 5.

Figure 3:
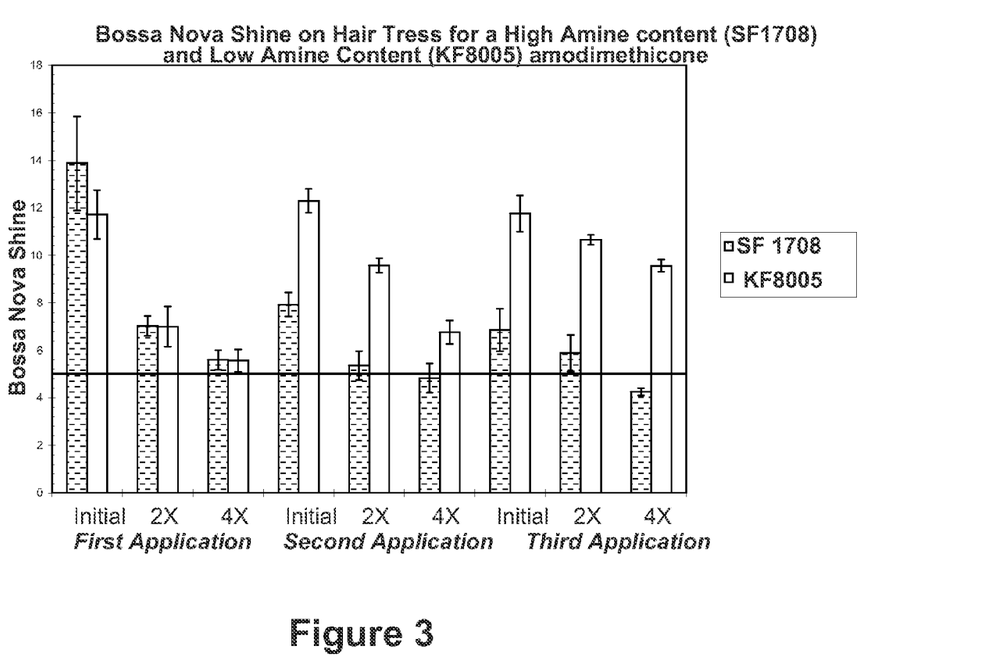
FIG. 3 shows Bossa Nova Shine on hair tresses for a high amine content and low amine content amodimethicone.

The results of the Boss Nova shine measurements for each of Samples 4 and 5 are shown in FIG. 3. As can be seen from FIG. 3, the shine imparted by Sample 5, which contains the SF1708 material, was significantly decreased after re-application of the hair care composition. In addition, it was observed that the hair samples twice or three times treated with Sample 5 felt tacky, heavy and looked matte, all of which are undesirable aesthetic properties for a hair care composition. In contrast, Sample 4, which contained the KF-8005 material, imparted a similar level of shine after each of the second and third application of Sample 4 to the hair samples.

In view of the data provided in FIGS. 2 and 3, it is believed that a hair care composition having aminosilicone having a viscosity from about 800 to about 1,600 mm²/s at 25° C., and a functional group equivalent weight from about 8,000 to about 14,000 g/mol, in particular the KF-8005 material, does not significantly build up on the hair after repeated applications and therefore, does not adversely impact the aesthetic appearance, particularly shine and feel of the hair.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

The invention claimed is:

1. A method for imparting a long-wearing shine to hair, comprising applying to the hair a composition comprising an aminosilicone polymer that has the structure:

where
x is an integer from 1 to 6,
y is an integer from 1 to 6, and
m and n are independently each an integer from 1 to 5,000 and are selected to provide a viscosity of about 1,200 mm²/s at 25° C., and a functional group equivalent weight (FGEW) of about 11,000 g/mol, and a suitable vehicle.

2. The method according to claim 1, wherein said aminosilicone polymer has a refractive index greater than 1.4 at 25° C.

3. The method according to claim 1, wherein x is 3 and y is 2.

4. The method according to claim 1, wherein said composition further comprises a film former.

5. The method according to claim 1, wherein said composition is substantially anhydrous.

6. The method according to claim 1, wherein said composition further comprises a shine enhancer.

7. The method according to claim 6, wherein said shine enhancer is an aryl-silicone having a refractive index greater than 1.4 at 25° C.

8. The method according to claim 6, wherein said shine enhancer is a phenyltrimethicone or dimethicone.

9. A hair care composition comprising:
(a) from about 1 to about 25 percent by weight of an aminosilicone polymer that has the structure:

where
x is an integer from 1 to 6,
y is an integer from 1 to 6, and
m and n are independently each an integer from 1 to 5,000 and are selected to provide a viscosity of about 1,200 mm²/s at 25° C., and a functional group equivalent weight of about 11,000 g/mol, and
(b) a suitable vehicle.

10. The composition according to claim 9, wherein said aminosilicone has a refractive index greater than 1.4 at 25° C.

11. The composition according to claim 9, wherein x is 3 and y is 2.

12. The composition according to claim 9, further comprising a shine enhancer.

13. The composition according to claim 12, wherein said shine enhancer is a phenyltrimethicone or dimethicone.

* * * * *